(12) United States Patent
Rao et al.

(10) Patent No.: US 7,390,462 B2
(45) Date of Patent: Jun. 24, 2008

(54) RATIOMETRIC FLUORESCENT PH SENSOR FOR NON-INVASIVE MONITORING

(75) Inventors: Govind Rao, Columbia, MD (US);
Iordan V. Kostov, Baltimore, MD (US);
Haley R. Kermis, Baltimore, MD (US);
Peter Harms, Ellicott City, MD (US)

(73) Assignee: The University of Maryland Baltimore County, Baltimore, MD (US)

( * ) Notice: Subject to any disclaimer, the term of this patent is extended or adjusted under 35 U.S.C. 154(b) by 569 days.

(21) Appl. No.: 10/609,720

(22) Filed: Jun. 30, 2003

(65) Prior Publication Data

US 2005/0090014 A1    Apr. 28, 2005

Related U.S. Application Data

(60) Provisional application No. 60/478,051, filed on Jun. 12, 2003, now abandoned, provisional application No. 60/434,034, filed on Dec. 17, 2002, now abandoned.

(51) Int. Cl.
| | |
|---|---|
| *G01N 21/00* | (2006.01) |
| *G01N 21/64* | (2006.01) |
| *G01N 21/66* | (2006.01) |
| *G01N 21/76* | (2006.01) |
| *G01N 33/50* | (2006.01) |
| *G01N 31/16* | (2006.01) |
| *G01N 31/22* | (2006.01) |
| *G01J 1/48* | (2006.01) |

(52) U.S. Cl. .................... 422/82.08; 422/82.05; 422/55; 422/86; 436/68; 436/163; 436/172

(58) Field of Classification Search ............. 422/82.05, 422/82.08, 55, 86; 436/68, 163, 172
See application file for complete search history.

(56) References Cited

U.S. PATENT DOCUMENTS 5,273,716 A * 12/1993 Northrup et al. ......... 422/82.07
6,485,703 B1 * 11/2002 Cote et al. ................... 424/9.1

* cited by examiner

*Primary Examiner*—Jill Warden
*Assistant Examiner*—Keri A Moss
(74) *Attorney, Agent, or Firm*—Benjamin Aaron Adler

(57) ABSTRACT

The present invention provides ratiometric fluorescent pH sensors for non-invasive, continuous monitoring of pH in such applications as fermentation processes. The ratiometric fluorescent pH sensors comprise a fluorescent dye that exhibits a shift in excitation wavelength with a corresponding shift in pH in the local environment of said fluorescent dye. Ratiometric measurements of the emission intensities at dual excitation maxima correlate to pH. Also provided is a fluorescent dye 6-methacryloyl-8-hydroxy-1,3-pyrene disulfonic acid (MA-HPDS). Further provided are systems and methods to non-invasively and continuously monitor pH.

27 Claims, 12 Drawing Sheets

RATIOMETRIC FLUORESCENT PH SENSOR FOR NON-INVASIVE MONITORING

CROSS-REFERENCE TO RELATED APPLICATIONS

This non-provisional application claims benefit of U.S. provisional application Ser. No. 60/478,051, filed Jun. 12, 2003, now abandoned and U.S. provisional application Ser. No. 60/434,034, filed Dec. 17, 2002, now abandoned.

FEDERAL FUNDING LEGEND

This invention was made with government support under contract No. 0091705 awarded by the National Science Foundation. The government has certain rights in the invention.

BACKGROUND OF THE INVENTION

1. Field of the Invention

The present invention relates in general to fluorescent pH sensors and ratiometric fluorescence measuring techniques. More particularly, the present invention relates to a fluorescent dual excitation-ratiometric pH sensor for non-invasive monitoring of pH.

2. Description of the Related Art

In recent years, there has been considerable research effort toward the development of techniques for continuous on-line monitoring of pH for environmental, biomedical and bioprocess applications. In particular, optical techniques based on fluorescence measurements offer many advantages over conventional electrochemical approaches including high sensitivity and ease of miniaturization. In addition, since fluorescence emission from an indwelling patch can be monitored without direct contact, in situ pH measurements can be made non-invasively with external instrumentation. The latter is highly desirable for bioprocesses using large, instrumented fermenters, by circumventing the cumbersome task of probe sterilization. For benchtop shake flasks and small scale, high throughput operations that do not readily accommodate the larger probes, in situ fluorescence-based patches delivering continuous real time pH values could be used to monitor and even control the acidity of the environment.

With judicious choice of the fluorescent indicator and immobilization conditions, measurements can be made over the desired region with high sensitivity. Sensors have been developed that measure the pH-dependent change in emission intensity, including those based on fluorescein, cyanine (1) and transition metal complexes (2-4). However, the inherent drawbacks of intensity-based measurements include signal variations due to probe photobleaching and fluctuations in source intensity, and sensitivity to position and orientation of the sensor patch that precludes non-invasive detection.

Furthermore, measurements in highly scattering or fluorescent media are difficult at best, even with an opaque membrane backing (5). Sensors based on the pH-dependent change in fluorescent lifetime of an immobilized ruthenium metal ligand complex (6) do not suffer the same drawbacks, but require more complicated instrumentation. In addition, sensitivity to collisional quenching by oxygen results in an additional calibration parameter or operation under anaerobic conditions.

An alternate approach that circumvents the problems associated with intensity-based measurements is ratiometric detection. Given a fluorescent indicator that exhibits a shift in excitation or emission wavelength with pH, the ratio of the emission intensity at the two wavelengths can be used as a robust measure of the pH that is insensitive to orientation, probe concentration and background fluorescence. Dual emission fiber-optic sensors based on seminapthofluorescein (7) and carboxynaphthofluorescein (8) have been described that rapidly and reliably correlate intensity ratios to pH. The extensive photobleaching that is observed for these dyes is accounted for by the ratiometric approach, but would still limit the useful lifetime of the sensor.

The fluorescent dye 8-hydroxy-1,3,6-pyrene trisulphonic acid trisodium salt (HPTS) consists of a pyrene core with three sulfonic acid groups and a hydroxyl group that imparts pH sensitivity around a pka of approximately 7.3 (9). HPTS exhibits two excitation wavelengths, one UV at 405 nm and one blue at 457 nm, that correspond to the acid and its conjugate base (9-10). The subsequent pH-dependent shift in excitation maximum about the pKa of 7.3 enables dual-excitation ratiometric detection in the physiological range. This, together with a low toxicity (11) and insensitivity to oxygen concentration (12), makes HPTS a suitable probe for physiological and bioprocess pH measurements.

To date, covalent attachment of HPTS has been via sulfonamide coupling (13). The presence of the three strongly anionic sulphonic acid groups allows for HPTS to be immobilized by ionic binding to cationic supports. While effective in immobilizing the dye and preserving pH sensitivity, polymer substrates are limited to those that contain primary amines. In addition, amine groups which remain on the substrate after coupling will affect the local pH inside the polymer matrix. The dye has been covalently attached to controlled pore glass (15) and aminoethyl cellulose (16) in the development of fluorescence-based pH sensors that operate in neutral and acidic environments, as well as an intravascular blood gas monitoring system where it was used for both pH and pCO2 detection (17). Fiber-optic pH sensors have been described with HPTS bound to an anion exchange membrane (12) or resin (18) and fixed to the tip of the optical fiber.

For example U.S. Pat. No. 5,114,676 provides a pH sensor with a fluorescent indicator which may be covalently attached to a particle or to a microcrystalline cellulose fiber. The sensor comprises an optically transparent substrate, a thermoplastic layer and a hydrogel. Part of the particle with the indicator attached thereto is imbedded in a thermoplastic layer that is coated on the substrate and mechanically adhered using heat and pressure. The majority of the particle/indicator is imbedded within a hydrogel layer that is applied over the thermoplastic layer. The pH sensor is applied to the tip of an optical waveguide.

Furthermore, with the recent availability of low cost UV LEDS, the dye can be measured with relatively inexpensive instrumentation that combines UV and blue LEDs and a photodiode module. Such a setup has been described (14) to detect the pH of a high throughput microbioreactor system via HPTS directly dissolved in the fermentation media.

The inventors have recognized a need for improvement in HPTS sensors and uses thereof in inexpensively collecting ratiometric emission data externally from a biosystem. Specifically, the prior art is deficient in sensors comprising HPTS or derivatives thereof which is easily immobilized in a polymer matrix having suitable optical and diffusion properties. Additionally, the prior art is deficient in the use of substrates other than those having substituent primary amines. Furthermore, the prior art is deficient in sensors comprising HPTS or derivatives thereof which are easily assembled and which can be used as indwelling sensors in a reaction vessel to collect ratiometric emission data. The present invention fulfills this long-standing need and desire in the art.

SUMMARY OF THE INVENTION

The present invention is directed to a fluorescent dye having the structure:

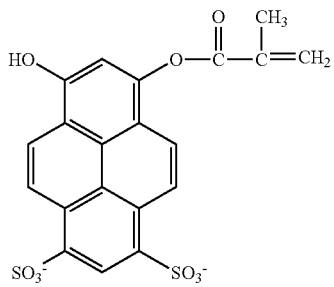

The present invention also is directed to a ratiometric fluorescent pH sensor comprising a fluorescent dye that exhibits a shift in excitation wavelength with a corresponding shift in pH in the local environment of the dye, a polymer matrix where the fluorescent dye can be immobilized therein, a means of optically isolating the polymer matrix comprising the fluorescent dye, and an adhesive means.

The present invention also is directed to a system for non-invasive monitoring of pH comprising a reaction vessel in which to monitor the pH, the ratiometric fluorescent pH sensor described herein whereby the adhesive means adheres the front surface of the pH sensor to the reaction vessel, a means for delivering a first pH-sensitive excitation maximum wavelength to the front surface of the fluorescent pH sensor; a means for delivering a second pH-sensitive excitation maximum wavelength to the front surface of the fluorescent pH sensor, a means for detecting maximum emission intensity of a wavelength emitted from the fluorescent pH sensor at both of the first and second pH-sensitive excitation maxima wavelengths, and a means for evaluating a ratio of the first and second maximum emission intensities as pH.

The present invention is further directed to a method of continuous monitoring of pH of a growth media during a fermentation process comprising placing the growth media or a sample therefrom into the reaction vessel of the system described herein. The fluorescent pH sensor is excited with the first of the pH-sensitive excitation maxima wavelengths and the intensity of fluorescent light emitted from the sensor at the emission maximum wavelength upon the first excitation is measured. The fluorescent pH sensor is further excited with the second of the pH-sensitive excitation maxima wavelengths and the intensity of fluorescent light emitted from the sensor at the emission maximum wavelength upon the second excitation is measured. A ratio of the emission intensity at the first excitation maxima wavelength to the emission intensity at the second excitation maxima wavelength is calculated and the ratio is correlated the pH of the growth media thereby monitoring pH during fermentation.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
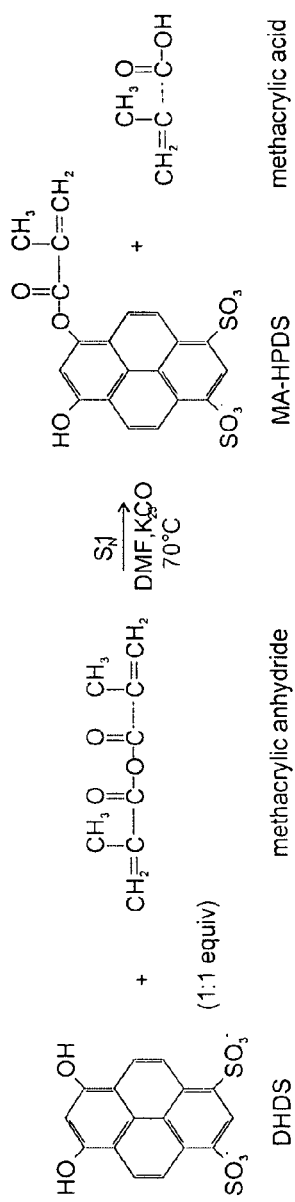
FIGS. 1A-1C depict the reaction schemes for the modification of 6,8-dihydroxy-1,3-pyrenedisulfonic acid (DHDS) to form 8-methacryloyl-6-hydroxy-1,3-pyrenedisulfonic acid (MA-HPDS) (FIG. 1A) and copolymerization of the modified dye with poly(ethylene glycol) diacrylate (PEG-DA) (FIG. 1B) and the schematic diagram of the sensor assembly using a HPDS-PEG copolymer hydrogel (FIG. 1C).

In one embodiment of the present invention there is provided a fluorescent dye having the structure:

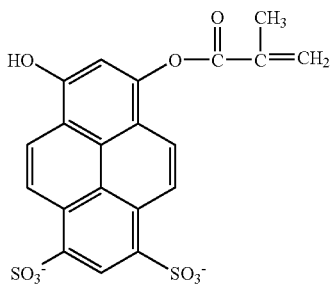

In this embodiment the fluorescent dye is 6-methacryloyl-8-hydroxy-1,3-pyrene disulfonic acid (MA-HPDS).

In another embodiment of the present invention there is provided a ratiometric fluorescent pH sensor comprising a fluorescent dye which fluorescent dye exhibits a shift in excitation wavelength with a corresponding shift in pH in the local environment of the fluorescent dye, a polymer matrix which immobilizes the fluorescent dye therein and where the polymer matrix comprises a front surface and a back surface, a means of optically isolating the polymer hydrogel comprising the fluorescent dye, and an adhesive means.

In one aspect of this embodiment the ratiometric fluorescent pH sensor comprises the fluorescent dye 6-methacryloyl-8-hydroxy-1,3-pyrene disulfonic acid (MA-HPDS). In this aspect the polymer matrix may comprise a p(ethylene glycol) hydrogel. The MA-HPDS covalently binds p(ethylene glycol) diacrylate in a polymerization reaction thus functioning as a comonomer and becoming immobilized within the p(ethylene glycol) hydrogel. Further to this aspect the fluorescent pH sensor additionally may comprise a comonomer and/or a cross-linking agent. The comonomer may be a siloxane-based monomer. The cross-linking agent may be trimethylolpropane triacrylate or ethylene glycol dimethacrylate.

In another aspect of this embodiment the ratiometric fluorescent pH sensor may comprise the fluorescent dye 8-hydroxy-1,3,6-pyrene trisulphonic acid trisodium salt (HPTS). The polymer matrix may comprise a p(ethylene glycol). The monomer p(ethylene glycol) diacrylate is polymerized around the anionic exchange resin to form the hydrogel. The anionic exchange resin immobilizes the HPTS within the hydrogel via ionic binding.

In yet another aspect of this embodiment the ratiometric fluorescent pH sensor again comprises the fluorescent dye HPTS. In this aspect the polymer matrix comprises a copolymer poly(2-hydroxyethyl methacrylate)-co-(methacryloyl ethyltrimethyl ammonium chloride) (pHEMA-METMA) hydrogel. The HPTS ionically binds to the copolymer thus becoming immobilized within the pHEMA-METMA copolymer hydrogel.

In all aspects of this embodiment the optically isolating means may be a microfiltration membrane. The adhesive means may be an adhesive tape, a hydrophobic adhesive substrate or a transfer adhesive. A representative example of adhesive tape is a polyethylene tape. An example of a hydrophobic adhesive substrate is a silicon rubber substrate or an acrylate-functional adhesive. Again in all aspects the fluorescent dye may exhibit dual excitation maxima and an emission maximum wavelength. Additionally, the fluorescent sensor responds to a shift in pH within a range of about pH 6.0 to about pH 9.0. Furthermore the fluorescent pH sensor may be sterilized.

Further to all aspects the sensor may comprise a patch. The sensor patch may be assembled by placing the adhesive means on a flat surface and adhering the front surface of the polymer matrix to the adhesive means. The back surface of the polymer matrix is covered with the optically isolating means. The adhesive means and the optically isolating means are as described supra.

In yet another embodiment of the present invention there is provided a system for non-invasive monitoring of pH comprising a reaction vessel in which to monitor the pH, the ratiometric fluorescent pH sensor described supra where the front surface of the pH sensor adheres to the reaction vessel via the adhesive means, a means for delivering a first pH-sensitive excitation maximum wavelength to the front surface of the fluorescent pH sensor, a means for delivering a second pH-sensitive excitation maximum wavelength to the front surface of the fluorescent pH sensor, a means for detecting maximum emission intensity of a wavelength emitted from the fluorescent pH sensor at both of the first and second pH-sensitive excitation maxima wavelengths, and a means for evaluating a ratio of the first and second maximum emission intensities as pH. This embodiment may further comprise means for closed-loop feedback control of the system.

In all aspects of this embodiment the ratiometric fluorescent pH sensors have the dual excitation maxima wavelengths and the emission maximum wavelength as described supra. An example of a delivery means is a light-emitting diode. The light-emitting diode may emit light in the UV range or in the blue wavelength range. A representative detecting means is a photodiode.

In still another embodiment of the present invention there is provide a method of continuous monitoring of pH of a growth media during a fermentation process comprising the steps of placing the growth media or a sample therefrom into the reaction vessel of the system described supra, exciting the fluorescent pH sensor with the first of the pH-sensitive excitation maxima wavelengths, measuring the intensity of fluorescent light emitted from the sensor at the emission maximum wavelength upon the first excitation, exciting the fluorescent pH sensor with the second of the pH-sensitive excitation maxima wavelengths, measuring the intensity of fluorescent light emitted from the sensor at the emission maximum wavelength upon the second excitation calculating a ratio of the emission intensity at the first excitation maxima wavelength to the emission intensity at the second excitation maxima wavelength, and correlating the ratio to the pH of the growth media thereby monitoring pH during fermentation. In all aspects of this embodiment the excitation and emission wavelengths and the ratiometric fluorescent pH sensors are as described supra.

The following terms shall be interpreted according to the definitions set forth below. Terms not defined infra shall be interpreted according to the ordinary and standard usage in the art.

As used herein, "polymer hydrogel" shall refer to a polymer matrix that absorbs water in an aqueous environment.

The present invention provides fluorescent excitation-ratiometric, non-invasive pH sensors and applications thereof, e.g., continuous on-line fermentation monitoring. The ratiometric approach is robust and insensitive to factors such as source intensity, photobleaching or orientation of the sensor patch. The pH sensors of the present invention are capable of timely and reversible pH measurement and demonstrate linearity and sensitivity over a physiologically and bioprocess-relevant range. Measurements may be made with external instrumentation and without direct contact with the patch and thus detection is completely non-invasive.

The external instrumentation comprises an inexpensive excitation light source and emission photodetector thereby significantly lowering the cost of the hardware used to monitor pH. An excitation light source may be UV or blue LEDs and light emitted by the dyes incorporated into the sensors are detected by a photodiode module. The components are inexpensive, and represent a simple and potentially portable way to obtain reliable, on-line pH information from a bioprocess without the use of an invasive probe or optical fiber. The sensor is easily adaptable to closed-loop feedback control systems.

Provided herein is a simple and raid method for the covalent incorporation of HPTS into the backbone of a polymer matrix used to prepare a pH sensor. Covalently linking the dye overcomes problems associated with ionic immobilization of HPTS within a polymer matrix. As such, a derivative of HPTS, 6-methacryloyl-8-hydroxy-1,3-pyrenedisulfonic acid (MA-HPDS), in which one of the sulfonate groups is replaced by a methacrylate moiety provides a dye capable of effecting covalent binding with a polymer hydrogel. The single-step synthetic method uses a related dye, 6,8-dihydroxy-1,3-pyrenedisulfonic acid disodium salt (DHDS), which is similar in structure to HPTS except for an additional hydroxyl group which replaces one of the sulfonic acid groups. As a result, the dye has a second pKa at approximately 8.5 (9).

Nucleophilic substitution of one hydroxyl group with methacrylic anhydride results in a methacryloyl functional dye (MA-HPDS). The pendant methacrylate group can participate as a monomer in free radical polymerization reactions and can thereby be incorporated into a number of substrates. Furthermore, the crude product yield from the synthesis need not be purified to remove unreacted DHDS or methacrylate. The choice of comonomer(s) determines the properties of the matrix and can be engineered for specific properties, e.g., mass transport, mechanical strength and biocompatibility. The co-monomer may be, although not limited to, poly(ethylene glycol) diacrylate (PEG-DA). Additionally, a novel method for assembling the sensor patch is described herein. Generally, the swollen hydrogel layer is sandwiched between a microfiltration membrane such as white polyethersulfone microfiltration membrane backing and a layer of transfer adhesive.

Comonomers containing anionic groups might be incorporated to improve proton transport through the hydrogel or to shift the local pH inside the hydrogel. Mechanical strength might be improved through the addition of siloxane-based monomers or crosslinking agents such as trimethylolpropane triacrylate or ethylene glycol dimethacrylate. The free radical polymerization reaction described herein is not limited to photochemical initiation. Other radical initiators might be considered including thermal (e.g. azobis(4-cyanovaleric acid)) and redox initiators (e.g. sodium metabisulfite/ammonium persulfate). Additionally, it is contemplated that this modification technique may be used with other dyes. Fluorescein indicators contain two hydroxyl groups that may participate in nucleophilic substitution reactions with methacrylic anhydride. For example, dichlorofluorescein with a pka of ~4 may be used to extend the working range of the sensor to a lower pH.

Other embodiments of the invention presented herein are contemplated. For example other means of attachment may be used including cyanoacrylate adhesives and heterofunctional crosslinkers. Additionally, the sensors may be sterilized by means such as ethylene oxide treatment provided the hydrogel is kept hydrated. Also, it is contemplated that a temperature-independent sensor may be constructed since emission intensities normally decrease with increasing temperature.

While the pH range overlapped by the sensor patches described herein is somewhat narrow, i.e., the sensors function well over the pH range of 6 to 9, it is suitable for many industrially-relevant microbial fermentations. Since many relevant bioprocesses operate at a lower pH, e.g., yeast or fungi, dyes with lower pKa's may be used to expand the range of operation for monitoring in the non-invasive manner presented herein. These include, but are not limited to, 2',7'-bis-(2-carboxyethyl)-5-(and-6)-carboxyfluorescein (BCECF) and 5-(and-6)-carboxy-2'-7'-dichlorodifluorescein which can both be detected ratiometrically or other probes such as Rhodol Green™ and the LysoSensor™ dyes (23).

Applicability for non-invasive bioprocess monitoring and effectiveness of the sensors was demonstrated using an HPTS patch assembled by polymerization of HPTS-Dowex bound resin beads into a highly swollen poly(ethylene glycol) hydrogel layer. The hydrogel layer serves to fix the Dowex resin in place but still promotes proton diffusion in the vicinity of the dye. Additionally, poly(ethylene glycol) hydrogels have excellent biocompatibility (19, 20). Lastly, a white microfiltration membrane backing provides an optical barrier between the sensing layer and the background media.

The HPTS-Dowex sensor was successfully used in a shake flask setup to provide continuous, on line measurements of the pH of an *E. coli* fermentation over a range of about pH 6 to about pH 9. The dual-excitation ratiometric measuring technique, combined with the presence of an opaque membrane backing for optical isolation, eliminates any interference from the nutrient broth and cells. The pH recorded by the sensor on line was in good agreement with samples measured off line with a conventional pH electrode. The HPTS-Dowex-PEG sensor is suitable for bioprocess monitoring and can be adapted for pH control with a decrease in thickness and corresponding response time. However, the manufacturing process may be cumbersome and the presence of the micron scale Dowex resin beads may lead to difficulties in measurement. These include background fluorescence and position-dependent signal intensity.

Alternatively, HPTS may be immobilized within a homogeneous co-polymer layer that is hydrophilic and contains cationic functional groups similar to those on the Dowex resin to ionically bind HPTS. The sensor layer is a copolymer of poly(2-hydroxyethyl methacrylate)-co-(methacryloylethyltrimethyl ammonium chloride) (pHEMA-METMA) that is synthesized by the bulk free radical polymerization of the monomers in the presence of a crosslinker, e.g., ethylene glycol dimethacrylate (EGDMA). The poly(alkylacrylate) family of polymers is well-suited to bioprocess applications. These polymers have a typically high thermostability, which enables steam sterilization and a resistance to hydrolysis, which eliminates potentially toxic degradation by-products (21). In addition, the high water content of pHEMA-METMA promotes proton diffusion and rapid response times.

Again the use of a high water-content layer to immobilize HPTS is advantageous for proton diffusion but may present difficulties associated with adhesion of this layer to a reaction vessel as was observed with the HPTS-Dowex sensor. Since the pHEMA-METMA layer is highly swollen, conventional adhesives are ineffective. Additionally, the hydrogel must be kept fully hydrated to prevent cracking precluding the use of adhesives with long cure times.

As an alternative, it is contemplated that a two-layer patch comprising a pHEMA-METMA sensor layer chemically attached to a second, hydrophobic adhesive layer may be used. Acrylate-functional adhesives and silicone rubbers are available (Gelest Inc.; Tullytown, Pa.) with pendant methacryloyl functional groups that participate in free radical reactions. If the HEMA-METMA reaction mixture is polymerized on such a substrate, the result is a two-layer composite with excellent adhesion between the two polymers. The pHEMA-METMA layer is fully hydrated while the adhesive layer is hydrophobic and remains "sticky".

The METMA comonomer contains a quaternary ammonium group that imparts cationic functionality on the polymer for uptake of the anionic HPTS. While the methacrylate polymers in general are known to be hydrolytically stable, the presence of the quaternary ammonium group has been shown to increase the susceptibility of the ester linkage to hydrolysis at elevated temperatures (22). Indeed, following an autoclave cycle, a loss of fluorescence was observed (~50%) indicating the possibility that the cationic group is cleaved and lost. As the remaining HPTS is fully responsive and sufficient for detection in the spectrophotometer it is further contemplated that a higher loading of HPTS in the pHEMA-METMA layer can be used for detection with less expensive instrumentation. It is also contemplated that alternate comonomers that impart cationic functionality to the polymer but eliminate the unstable ester linkage be used, such as ar-(vinyl benzyl) trimethyl ammonium chloride.

The HPTS-pHEMA-METMA sensor described herein immobilizes the dye within a cationic matrix via ionic binding. However, while this immobilization strategy is sufficient for use in most buffer solutions, long term leaching of the dye can occur. Furthermore, ionic immobilization precludes the use of media containing strong anions, including the common cell culture media component Phenol Red that is used as a visual indicator of pH. Since Phenol Red contains sulfonic acid groups, it competes with HPTS for the cationic sites on the resin. This results in rapid loss of HPTS to the media causing signal loss over time until the sensor is no longer useable.

As described herein, the invention provides a number of therapeutic advantages and uses. The embodiments and variations described in detail herein are to be interpreted by the appended claims and equivalents thereof. The following examples are given for the purpose of illustrating various embodiments of the invention and are not meant to limit the present invention in any fashion.

EXAMPLE 1

Materials

The fluorescent dye 8-hydroxy-1,3,6-pyrene trisulphonic acid trisodium salt (HPTS) was obtained from Molecular Probes Inc. (Eugene, Oreg.). 6,8-dihydroxy-1,3-pyrenedisulfonic acid disodium salt (DHDS) was urchased from Fluka (Milwaukee, Wis.). Methacrylic anhydride (94% purity), anhydrous dimethyl formamide (DMFP, otassium carbonate and phenolsulfonephthalein sodium salt (Phenol Red) were purchased from Sigma-Aldrich Inc. (St. Louis, Mo.). Poly (ethylene glycol) diacrylate with an average molecular weight of 4000 was obtained from Polysciences Inc. (Warrington, Pa.). The photoinitiator Darocur® 1173, was supplied by Ciba Specialty Chemicals (Tarrytown, N.Y.).

Dowex 1×8-400 strongly basic anion exchange resin was obtained from Sigma Chemical Co. (St. Louis, Mo.). White microfiltration membranes in mixed esters of cellulose with a nominal pore diameter of 0.2 μm (Kimble) were used to optically isolate the sensor and as a support backing. The monomer 2-hydroxyethyl methacrylate (HEMA), initiator 2,2-dimethoxy-2-phenyl acetophenone (DMPA) and crosslinker ethylene glycol dimethacrylate (EGDMA) were obtained from Sigma-Aldrich (St. Louis, Mo.). The co-monomer methacryloyl ethyl trimethylammonium chloride (METMA) was obtained from Polysciences Inc. (Warrington, Pa.) as a 70% v/v aqueous solution.

Analytical grade sodium chloride, sodium dihydrogen phosphate and tris(hydroxymethyl)aminomethane (Tris) were obtained from Sigma Inc. (St. Louis, Mo.). Tryptone and yeast extract (Difco) used in the preparation of nutrient broth were from Beckton-Dickinson (Sparks, Md.).

EXAMPLE 2

Fermentation

The overnight seed culture consisted of a 1% inoculum of *Escherichia coli* JM105 strain frozen stock in 20 mL LB nutrient broth, incubated at 37° C. with shaking at 260 rpm (Orbit Environ Shaker, Lab-line Instruments, Melrose Park, Ill.). The fermentation was carried out at room temperature in a 500 mL shake flask containing 100 mL of LB broth that was inoculated with 2.5% seed culture. The shake flask was placed on a rotating shaker (LaPine Scientific Co., Berkeley, Calif.) set at 100 rpm. Dissolved oxygen and pH were not controlled.

EXAMPLE 3

Synthesis of
6-methacryloyl-8-hydroxy-1,3-pyrenedisulfonic acid
(MA-HPDS)

The indicator DHDS (100 mg) was dissolved in DMF (10 mL) in a 25 mL reaction vessel. Potassium carbonate (1 g) and methacrylic anhydride (1:1 eq., 36 μl L) were added. The vessel was stoppered and placed in a 70° C. water bath to react for 12 hours. The cooled reaction mixture was filtered. The solvent was removed from the filtrate in a rotary evaporator to yield the crude solid product (MA-HPDS).

Presumably, this product contains a mixture of the modified dye MA-HPDS with an unknown amount of reaction by-products that include unmodified DHDS and methacrylic acid salts. Further purification is unnecessary prior to copolymerization of the modified dye MA-HPDS and poly(ethylene glycol) diacrylate (PEG-DA). The reaction scheme is depicted in FIG. 1A.

EXAMPLE 4

Copolymerization of MA-HPDS with Hydrogel Monomer

A stock solution of MA-HPDS in deionized water (10 mg/mL) was prepared. Polymer precursor solution was prepared by combining 45 mg of PEG-DA, 200 μl of deionized water, 100 μl of the HPDS-MA stock solution and 6 μl of the photoinitiator Darocur and vortexing for 30 minutes. The precursor solution was polymerized between glass plates to prevent oxygen inhibition and volume contraction of the gel. Thickness was controlled with 2-inch wide, 0.004-inch thick aluminum spacer tape (McMaster-Carr Inc.; Atlanta, Ga.). Free radical polymerization of the acrylate end groups was initiated by exposure to a 100-W long wave UV spot lamp (UVP Inc.; Upland, Calif.) for 4 minutes. After polymerization, the PEG-HPDS layer was peeled from the glass plate and hydrated in deionized water for at least 48 hours. This both hydrates the matrix and removes any unbound dye. The resulting hydrogel layers were approximately 120 um thick.

Figure 1B:
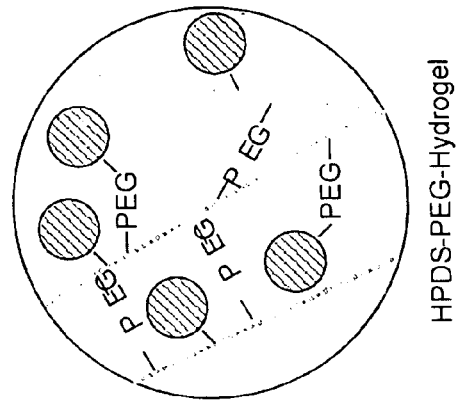
Figure 1B:
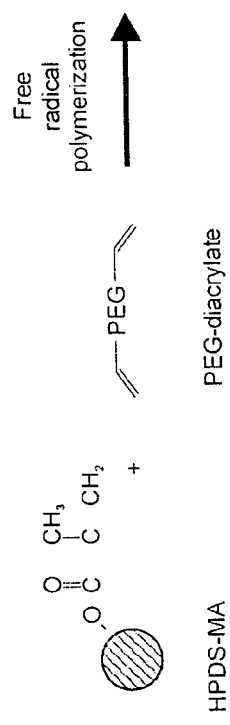

Any residual DHDS is free to diffuse out of the polymer matrix. This separation is readily accomplished in aqueous buffer because of the high water solubility of DHDS. Any methacrylic acid in the crude product will also be incorporated into the backbone of the polyme matrix and does not interfer with the spectral or pH behavior of the indicator. In order to verify modification of the dye and covalent attachment to the hydrogel matrix, the fraction of MA-HPDS in the crude product was estimated through measurement of the amount of dye that remained in the polymer matrix after extensive washing in buffer solution. These sensors were placed in phosphate-buffered saline at pH 7.2 and monitored for fluorescence over several days, with frequent changes of the soaking solution. After 10 days of soaking in aqueous buffer, the copolymer of PEG DA and MA-HPDS lost 26.7±3.3% of its original fluorescence intensity with the greatest loss of 20.8±6.5% occurring in the first 24 hours. Beyond this time fluorescence of the copolymer remained relatively stable. The fraction of dye retained in the matrix is a crude indicator of the conversion of the substituion reaction as it includes dye that is both covalently and nonspecifically bound. It is contemplated to increase the yield by optimizing the ratio of methacrylic anhydride to DHDS beyond the 1:1 equivalent used herein. Copolymerization is schematically depicted in FIG. 1B.

EXAMPLE 5

HPDS-PEG Sensor Assembly

The polymer hydrogel layer with the indicator dye covalently attached was fashioned into a sensor patch to facilitate testing. The polymer hydrogel layer was sandwiched between a bottom layer of transfer adhesive (Adhesives Research Inc.; Glen Rock, Pa.) and a top layer of white polyethersulfone microfiltration membrane (0.45 um, Pall Life Sciences; Port Washington, N.Y.). A 0.8×0.8 cm square was cut from the transfer adhesive and placed, liner down, on a flat surface. A smaller square of HPDS-hydrogel was blotted dry and placed in the center of the adhesive.

Figure 1C:
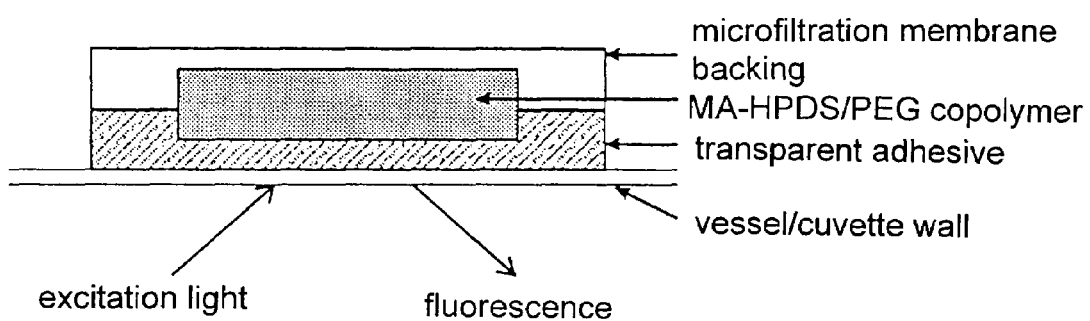

Immediately, the hydrogel was covered with a piece of white microfiltration membrane large enough to overlap the hydrogel and form a seal with the exposed edges of the adhesive. The opaque backing serves as an optical barrier between the sensing layer and the background solution, but still allows diffusion of protons. This is a critical component for the sensor's use in bioprocesses where culture media that is often colored and fluorescent will interfere with the optical signal from the dye. The liner was removed from the adhesive and the patch was secured to the inside wall of a cuvette for testing. A schematic diagram of the sensor patch is depicted in FIG. 1C.

EXAMPLE 6

Instrumentation and HPDS-PEG Sensor Evaluation

Fluorescence measurements were recorded with a Varian Cary Eclipse fluorescence spectrophotometer. A solid sample/cuvette holder designed for front-face measurements was used to measure sensor patches that were fixed to the inside front wall of a PMMA disposable cuvette. Excitation light was fixed at an angle of incidence of 30°. Solutions were measured in regular 90° configuration. Cuvettes containing sensor patches were equilibrated in buffered saline solutions ranging in pH from 5 to 10. Uncorrected excitation and emission spectra were recorded for each sample. For comparison, solutions of DHDS and HPTS were also prepared and tested at the same pH values.

EXAMPLE 7

Excitation and Emission Spectra for DHDS, HPTS and the Immobilized HPDS

Figure 2A:
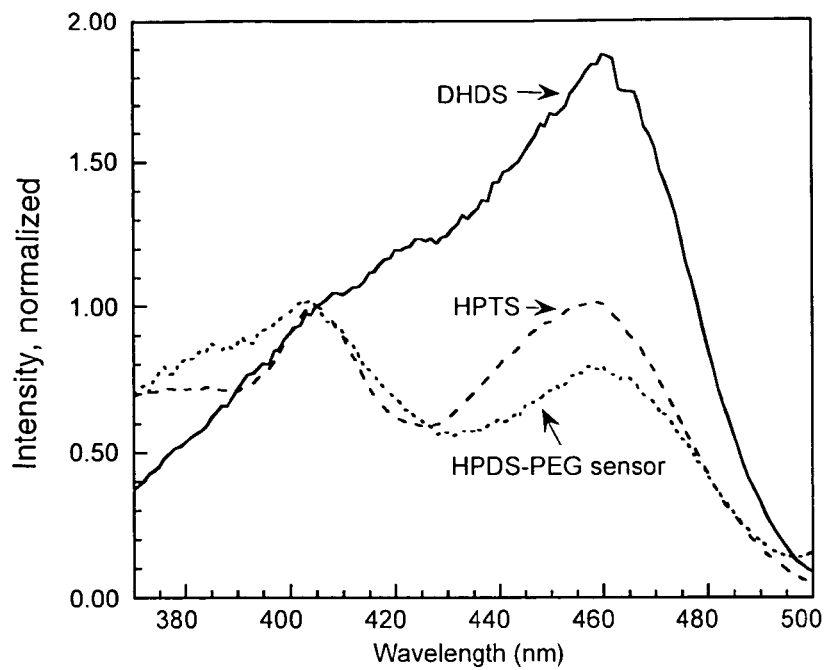
FIGS. 2A-2B depict the excitation (FIG. 2A) and emission (FIG. 2B) spectra of DHDS solution (1 μM), HPTS solution (1 μM) and HPDS-PEG sensor. Conditions are pH 7.2, 0.15 M PBS buffer and T=25° C.
Figure 2B:
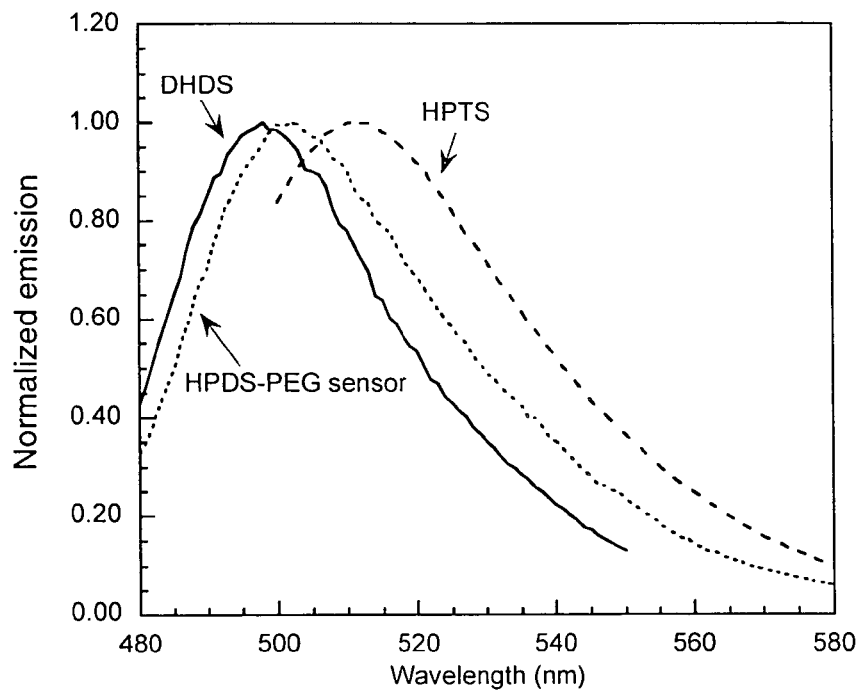

The excitation and emission spectra for DHDS, HPTS and the immobilized HPDS are shown in FIGS. 2A-2B. These three dyes are closely related with similar core construction but different pendant groups imparting functionality and, as such, their spectral behavior is similar. The excitation spectrum of the methacrylate-modified dye closely resembles that of HPTS. The immobilized dye exhibits excitation maxima at 404 nm and 457 nm corresponding to the acid and conjugate base, respectively.

As with HPTS, the acid-base equilibrium of the modified dye results in a pH-dependent change in the excitation spectrum toward increased blue excitation at higher pH. At the fixed pH of 7.2 DHDS exhibits relatively greater absorbance in the blue region, 460 nm, because of the second hydroxyl group on the pyrene core. The emission spectrum of the modified dye closely resembles that of HPTS and DHDS, with a single emission maximum at 502 nm. The relative locations of the emission maxima for these dyes may be subject to environmental effects in the polymer hydrogel matrix.

EXAMPLE 8

Figure 3:
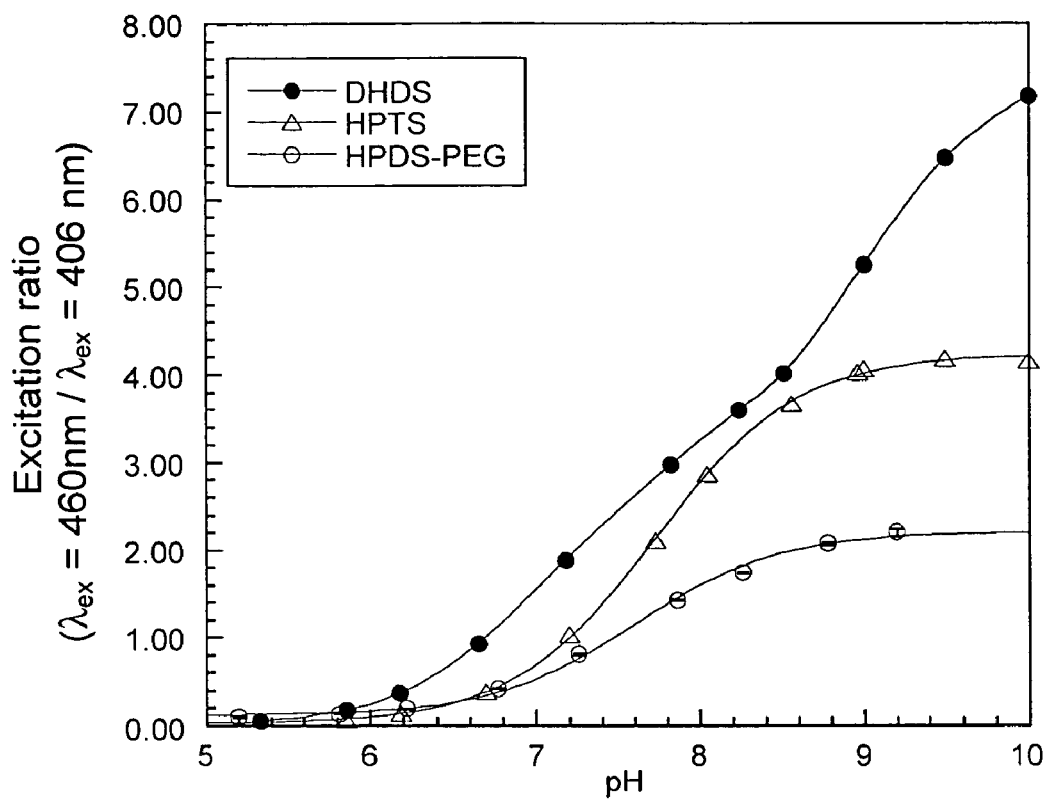
FIG. 3 depicts the calibration curves for DHDS solution (1 μM), HPTS solution (1 μM) and HPDS-PEG sensor. Conditions are 0.15 M buffers and T=25° C.

Calibration Curves of Excitation Intensity Ratio Versus pH for HPDS Solution, HPTS Solution and the Immobilized HPDS FIG. 3 depicts the calibration curves of excitation intensity ratio versus pH for DHDS solution, HPTS solution and the immobilized HPDS. Sensors comprising HDPS-PEG layers were calibrated in buffered saline solutions that ranged in pH from 5 to 10. In each case, the appropriate buffering species, i.e., phosphate, tris or bicarbonate, was at 10 mM and the desired ionic strength, e.g., 20, 150 or 300 mM, was made up with sodium chloride salt. Cuvettes containing sensor patches were equilibrated in each solution. For comparison 1 μM solutions of DHDS and HPTS also were prepared and tested over the same pH range.

Calibration curves for HPTS and MA-HPDS were fit to the following expression (25) describing intensity ratio (R) of monoprotic indicator dyes as a function of pH:

$$R = ([H^+]R_{max} + k_{a,app}R_{min})/k_{a,app} + [H^+] \tag{1}$$

where $k_{a,app}$ is the apparent dissociation constant of the immobilized dye. A least-squares linear regression was used to determine the parameters $R_{min}$, $R_{max}$ and $k_{a,app}$. The $pk_{a,app}$ of the immobilized dye was calculated to be 7.61±0.05 for these conditions. This is in good agreement with the $pk_{a,app}$ of HPTS in solution, which was calculated to be 7.72±0.02 under the same conditions.

The modified dye is sensitive over the same range as HPTS. The calibration curve for DHDS was fit to an expression similar to that for monoprotic acids, but for diprotic acids. The second hydroxyl group causes DHD to be sensitive over an extended range with two dissociation constants calculated to be $pk_{a1,app} = 7.03 \pm 0.02$ and $pk_{a1,app} = 9.05 \pm 0.02$ under these conditions. The calibration curve for MA-HPDS exhibits only a single inflection point and does not demonstrate sensitivity in the upper pH region >9. This further indicates that the substitution reaction has successfully modified the additional hydroxyl group.

Figure 11:
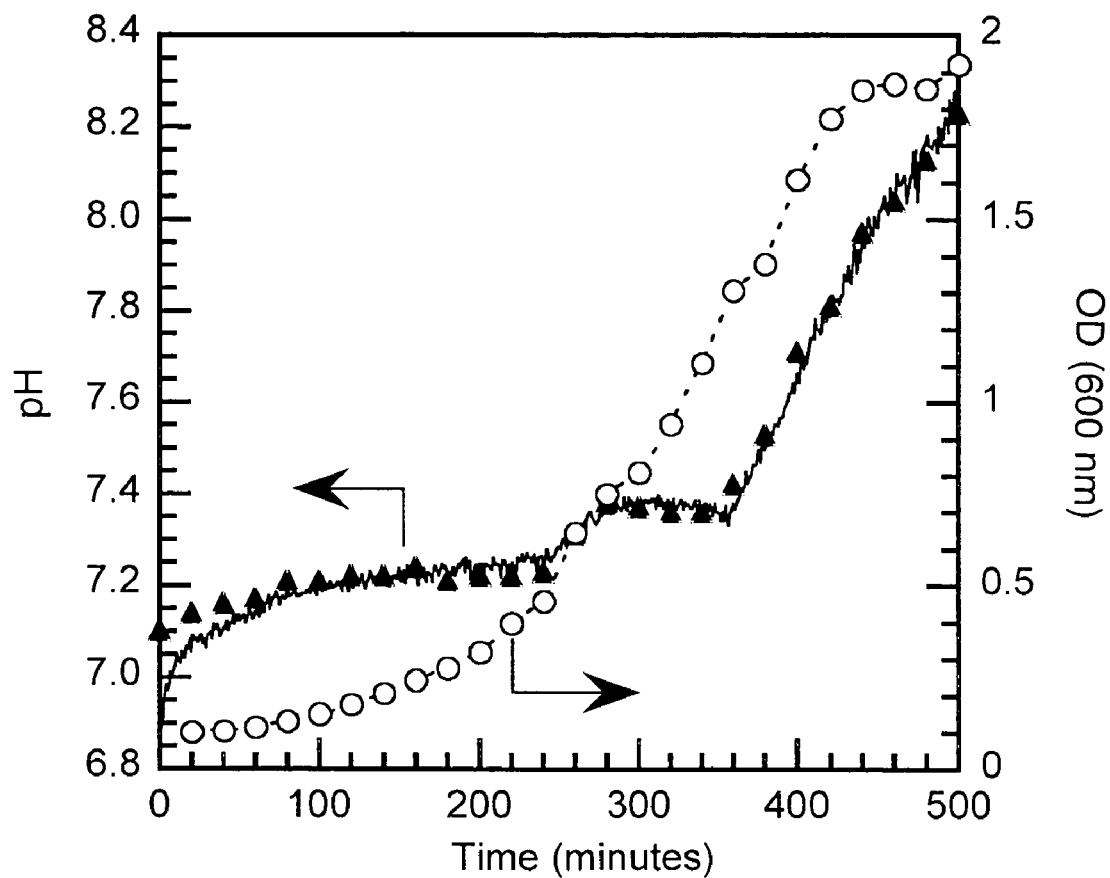
FIG. 11 depicts optical density measured at OD600 nm (O) and pH measured on-line by the sensor (–) and off-line with an ISFET pH probe (▲) during an *E. coli* fermentation.

The calibration curve for MA-HPDS depicted in FIG. 11 represents the average of three, separately constructed sensors. The reproducibility of the sensors is evidenced by the low standard error of <0.10 pH units over the range of sensitivity between pH 6 and 9. In addition, the response of the sensor is fully reversible and rapid, with 90% of the full response achieved within 3 minutes.

EXAMPLE 9

Sterilizing the HPDS-PEG Sensor

An additional advantage of HPDS-PEG sensors over those utilizing electrostatic immobilization to a resin is that the components are fully autoclavable. The poly(alkyl acrylate) family of polymers have a typically high thermostability which enables steam sterilization and a resistance to hydrolysis which elimates potentially toxic degradation by-products (21). Sensor assemblies were fixed to the inside of a glass vessel, covered with pH 7.2 buffer and autoclaved. Minimal loss of dye was observed and sensors remained intact and fixed to the wall.

However, a volume transition at the elevated temperature resulted in a reversible shrinking of the gel matrix between the membrane backing and the adhesive base. Upon rehydration, the gel layer did not return to its original configuration but remained somewhat "crinkled". The pH sensitivity and function of the sensor was preserved. This effect may be prevented by covalently coupling the hydrogel matrix to the adhesive base in order to minimize lateral contraction.

EXAMPLE 10

Ionic Strength Dependence of MA-HPDS Sensors

Figure 4A:
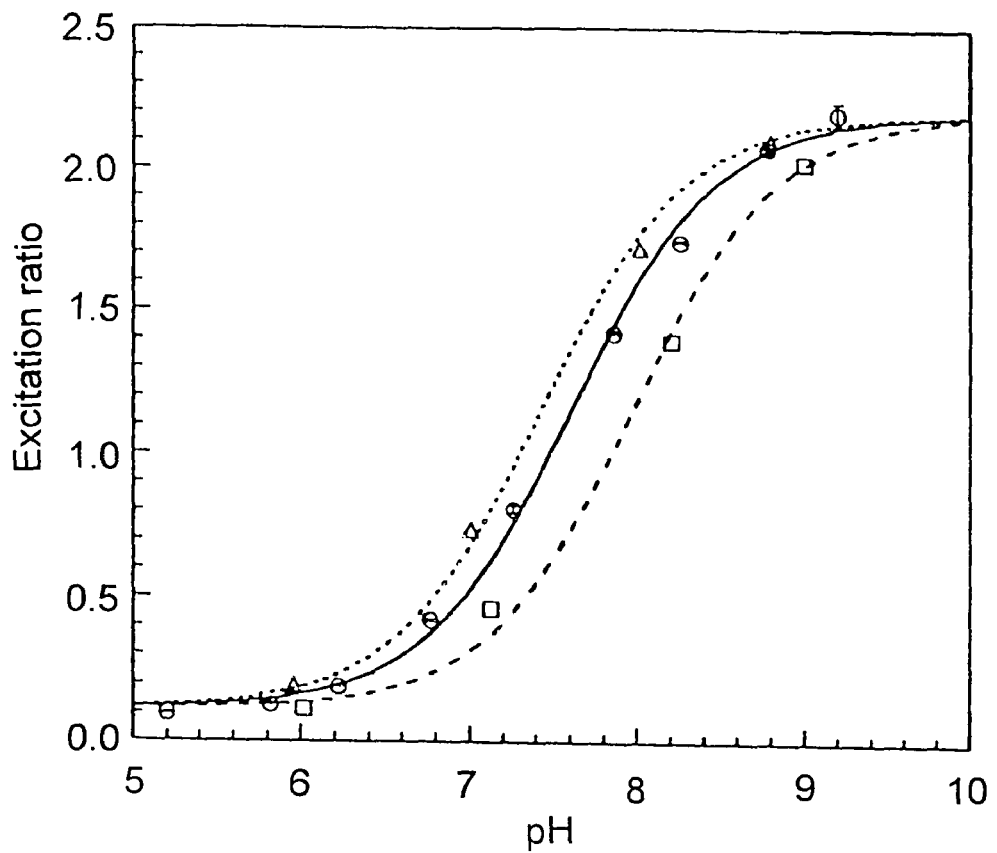
FIGS. 4A-4B depict the calibration curve for the HPDS-PEG sensor in 30 mM (Δ), 150 mM (O) and 300 mM (□) buffer (FIG. 4A) and the effect of buffer ionic strength on the $pk_{a,app}$ of the immobilized dye as described by equation 2 (FIG. 4B).
Figure 4B:
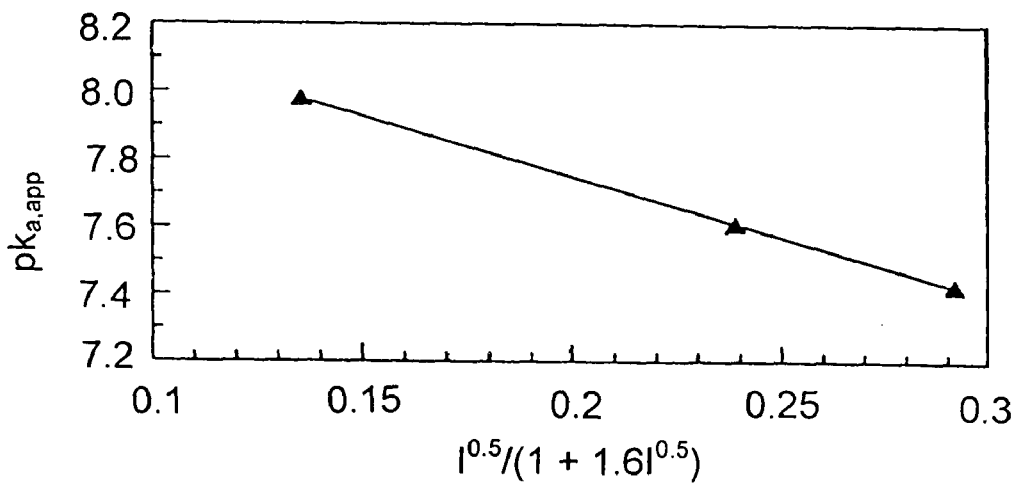

Because of its highly charged nature, HPTS is sensitive to changes in local ionic strength (15), as is methacrylate-modified dye, MA-HPDS. FIG. 4A depicts the ionic strenth dependence of sensor assemblies prepared with MA-HPDS in PEG-DA. A change in ionic strength has no effect on the range of the sensor, but does result in a small shift in the apparent pka of the immobilized dye. The pka of the dye at each ionic strenth was calculated using equation 1. Weak acid dissociation is afected by ionic strength according to the following equation 2 (28):

$$pK^I_a = (pK^{th}_a + 0.512(z_A^2 - z_{HA}^2)) \times (I^{0.5}/I + 1.6I^{0.5}) \qquad (2)$$

where $pKa^{th}$ is the thermodynamic pka of the dye, $z_A$ and $z_{HA}$ are the charges on the acid and the conjugate base respectively and I is the ionic strength of the buffer. This relationship arises due to changes in the activity of the electrolyte species. The ionic strength dependence of the immobilized dye over the observed range of 30-300 mM is well described by equation 2, as demonstrated by the linearity of the plot in FIG. 4B. In the case of bioprocess control schemes, should the ionic strength change enough to warrant recalibration, the new parameter could be predicted using this equation.

EXAMPLE 11

HPDS-PEG Emission Intensity in Phenol Red Solution

Sensor patches containing MA-HPDS copolymerized with PEG-DA were equilibrated in pH 7.2 buffer with 150 mM ionic strength containing 0.01 g/L Phenol Red. A slight loss of emission intensity, i.e., 16.6±2.0%, was observed, owing to the absorbance of the Phenol Red dye in the wavelength region under investigation, however the intensity ratio remained constant. The signal loss was reversible and returned to the original value within 3.6% when the sensor was returned to clear buffer (data not shown).

EXAMPLE 12

Instrumentation and Sensor Evaluation HPTS-Dowex-PEG Sensor

Fluorescence measurements were performed using a Varian Cary Eclipse fluorescence spectrophotometer with a solid sample/cuvette holder designed for front-face measurements with excitation light at an angle of incidence between 20 and 35 degrees. Excitation and emission spectra of both solutions and sensor assemblies were recorded in polystyrene disposable cuvettes fixed at 20 degrees from the incident beam. For measurement of the HPTS-Dowex-PEG sensor, the assembly was mounted to the inside front surface of the cuvette using double-sided adhesive tape. Unless otherwise stated, all measurements were performed at room temperature (25+/−2° C.).

In order to measure the response time of the sensor, buffer solutions were continuously pumped from larger reservoirs into a sealed cuvette containing a sensor assembly, using a peristaltic pump operated at 40 mL/min. At this flow rate, the well-stirred solution, ~4 ml, inside the cuvette would be replaced in approximately 40 seconds (6τ).

Since the solid sample/cuvette holder is not equipped for temperature control, a separate single-cell Peltier accessory was used to collect excitation spectra at temperatures other than ambient. Temperature control in the jacket surrounding the cuvette was varied between 10° C. and 40° C. Since the single-cell Peltier unit is not adaptd for front-face measurements, the sensor assembly was suspended in the cuvette from a rubber stopper at 20 degrees from the incident beam.

EXAMPLE 13

HPTS-Dowex-PEG Sensor Fabrication

The Dowex resin beads used to immobilize HPTS consist of a polystyrene support with quaternary ammonium groups capable of ionic binding with the sulphonic acid groups of HPTS. One gram of Dowex resin was suspended in 10 mL of a 50 μM solution of HPTS in deionized water. The resin suspension was allowed to equilibrate at room temperature for 24 hours with occasional stirring. Polymer precursor solution was prepared by combining 50 mg PEG-diacrylate, 0.2 mL of the HPTS-Dowex suspension and 2 μL Darocur® and vortexed for 10 minutes. The precursor solution was polymerized directly onto the membrane backing to promote adhesion and between glass slides to prevent oxygen inhibition. The beads are then physically entrapped in a hydrogel layer formed by the free radical polymerization of poly(ethylene glycol) diacrylate. The resulting matrix is highly swollen, at approximately 85% water contend (26) and promotes proton diffusion.

Specifically, the microfiltration membrane was cut to 2 cm×4 cm and placed on a glass microscope slide. The precursor solution was pipetted directly onto the membrane backing and covered with a second glass slide, using aluminum spacer tape at the edges to control the gap thickness. Free radical polymerization of the acrylate end groups was initiated by exposure to a 100 W long wave UV spot lamp (UVP, Inc., Upland, Calif.) for 30 seconds. After polymerization, the peg-Dowex layer was peeled from the glass slides with the microfiltration membrane attached to the bottom surface and allowed to hydrate in deionized water for 24 hours. Sensors constructed in this manner were approximately 250 μm thick. For comparison, control PEG-Dowex layers without HPTS were also prepared.

EXAMPLE 14

Recording of Fluorescence Spectra to Reduce Scatter and Reflection

To facilitate insertion of the sensor into cuvettes for reproducible analysis, the HPTS-Dowex-PEG layer was affixed to rigid transparency film. A 0.8 cm square of hydrogel was blotted dry and placed backing-up on a transparency film. The layer was fixed to the surface with black polyethylene waterproof tape (3M, St. Paul, Minn.) from which a 0.5 cm square had been removed to provide exposure to the sample solution. With this setup, the sensor assembly could be easily attached to the inside surface of polystyrene disposable cuvettes using adhesive or double-sided tape, enabling front face measurement of the HPTS-Dowex-PEG layer.

Figure 5:
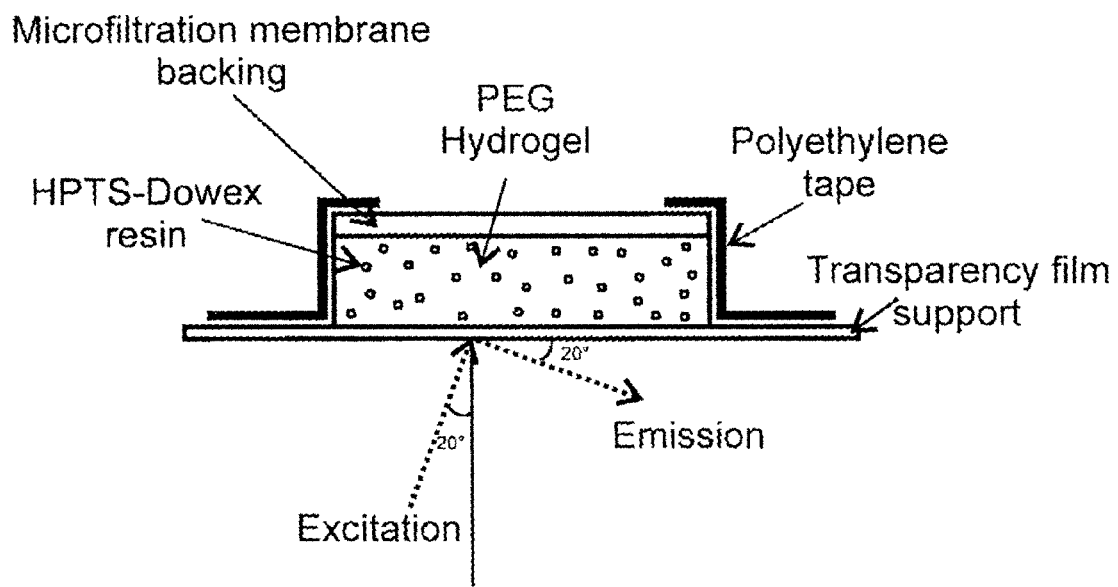
FIG. 5 illustrates the sensor assembly affixed to transparency film.

As depicted schematically in FIG. 5, fluorescence spectra were recorded with the sensor fixed at 20 degrees from the excitation beam. This configuration was chosen by comparison of the excitation spectrum for HPTS solution at 90 degrees with the spectra collected in the solid sample/cuvette holder at incident angles between 20 and 35 degrees. At 20 degrees, scatter and reflection were reduced with minimal loss of emission intensity.

EXAMPLE 15

HPTS-Dowex-PFG Sensor Calibration

For calibration of the sensor assemblies, buffered saline solutions (0.15 M or 0.3 M overall ionic strength) were prepared by reconstitution of sodium chloride and the appropriate base (10 mM) in deionized water and titration to the desired pH using 1 M HCl or 1M NaOH. Calibration buffers with pH between 6.2 and 8.2 were buffered with phosphate, while those solutions of higher pH (>8.2) were buffered with Tris. Luria-Bertani (LB) nutrient broth was prepared that contained sodium chloride (5 g/L), tryptone (10 g/L) and yeast extract (5 g/L) with pH adjusted to 7.2 with strong acid or base. The pH of each solution was recorded using a Model IQ240 Benchtop/Portable ISFET sensor pH probe (IQ Scientific Instruments; San Diego, Calif.).

EXAMPLE 16

Figure 6A:
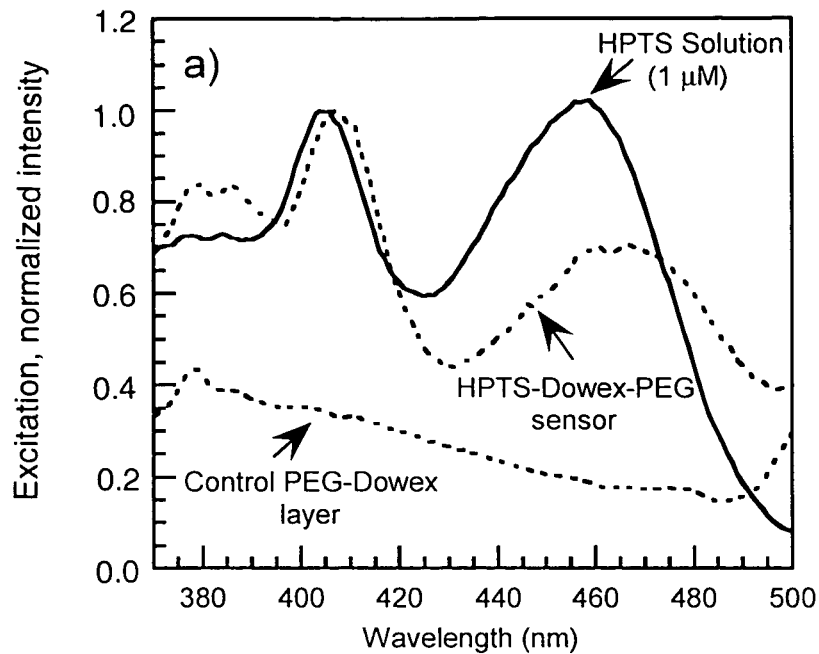
FIGS. 6A-6B depict the normalized excitation spectra (λemission=515 nm) (FIG. 6A) and the normalized emission spectra (λexcitation=408 nm) (FIG. 6B) of 1 μM HPTS solution, HPTS-PEG-Dowex sensor and control PEG-Dowex sensor in pH 7.2 0.15M PBS.
Figure 6B:
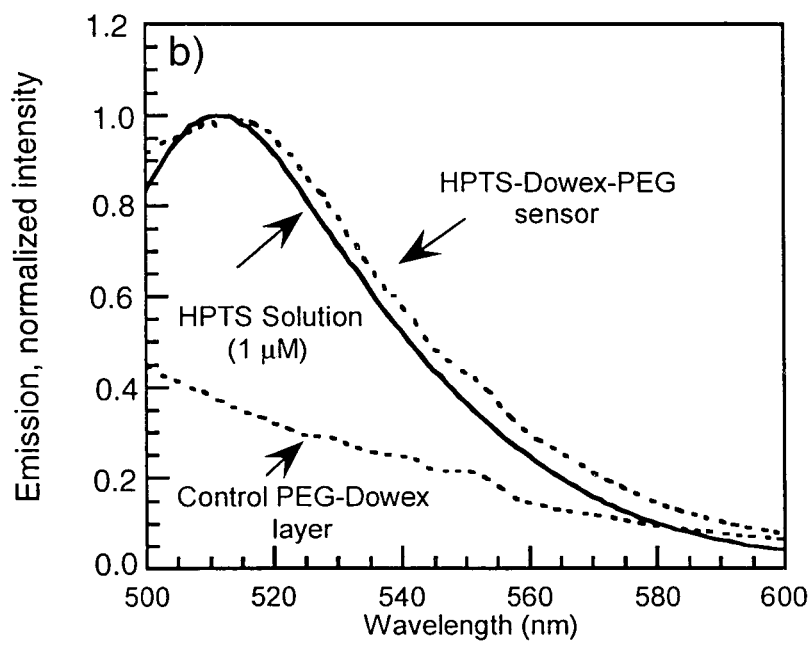

Comparison of HPTS and HPTS-PEG-Dowex Sensor Assembly Excitation and Emission Spectra FIGS. 6A and 6B compare the excitation and emission spectra of HPTS solution and HPTS immobilized in the PEG-Dowex matrix, both in pH 7.2 buffer. In the immobilized form, the two characteristic pH-sensitive excitation wavelengths of HPTS are preserved, however, both the excitation and emission maxima are slightly red-shifted to 408 nm, 468 nm and 515 nm, respectively. This effect has been observed for HPTS immobilized on Dowex anion exchange resin (24). In addition an increase in emission intensity with excitation at the UV wavelength relative to the blue wavelength is observed for the immobilized dye. This may be attributed to background fluorescence and scatter from the PEG-Dowex matrix.

The excitation spectra of the control layer prepared without HPTS is also depicted in FIG. 6A and shows preferential excitation in the UV region. The white membrane backing on the sensor patch also contributes to the measured scatter and reflection, although this is minimized with the sensor orientation fixed at 20 degrees from the excitation beam. Similar membranes have been stained black to circumvent this difficulty (5). However, the presence of the white, reflective surface serves to enhance the signal output from the sensor by reflection of both incident and emitted light back through the HPTS layer, rather than allowing transmission beyond the patch. This effectively doubles the path length of the beam, resulting in emission intensities that are considerably, up to 4 times, higher than those from similar sensors with no membrane backing (data not shown).

EXAMPLE 17 pH-Dependent Excitation Spectra of HPTS-PEG-Dowex Sensor Assemblies

Figure 7A:
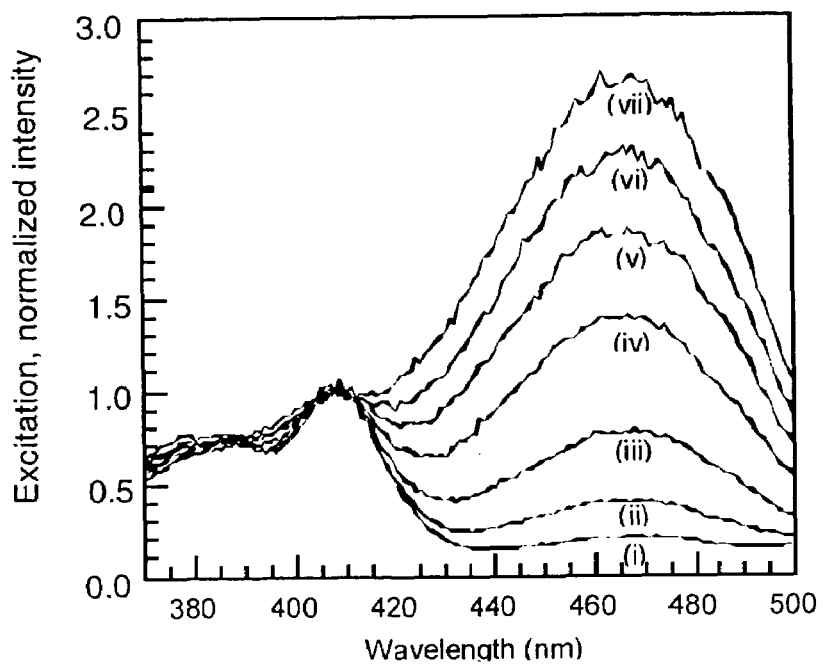
FIGS. 7A-7B depict the normalized excitation spectra (λemission=515 nm) of HPTS immobilized in the PEG-Dowex sensor at pH: (i) 6.2, (ii) 6.69, (iii) 7.16, (iv) 7.66, (v) 8.0, (vi) 8.42 and (vii) 8.81 (FIG. 7A) and the intensity ratio of the sensor measured at 515 nm ((λex=468 nm/λex=408 nm) in 0.15 M PBS (FIG. 7B).
Figure 7B:
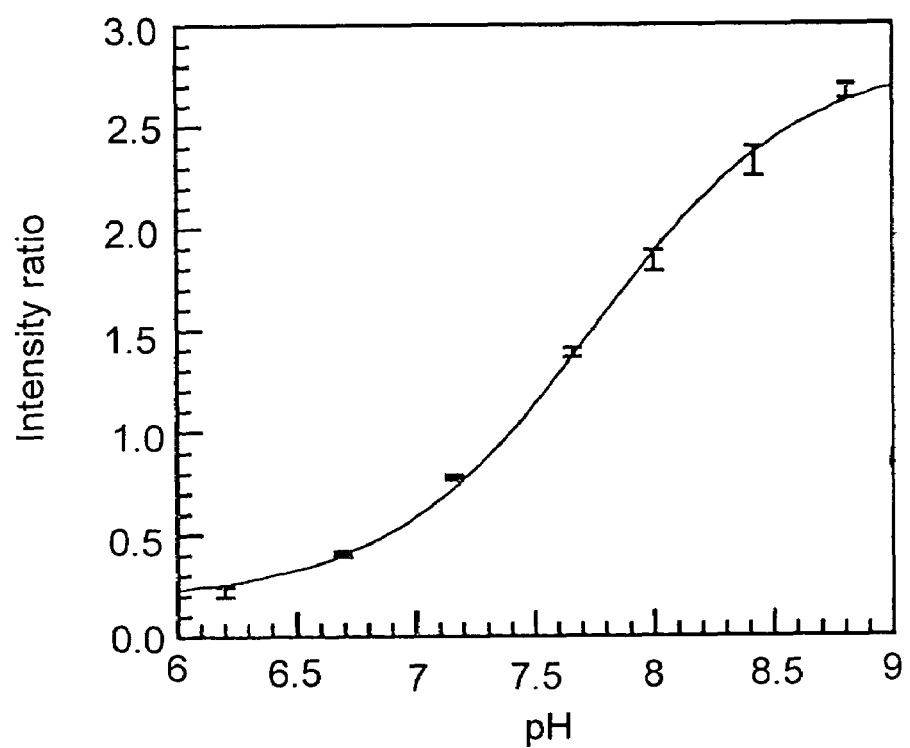

FIG. 7A depicts the pH-dependent excitation spectra of HPTS-Dowex-PEG sensor assemblies measured at a fixed emission wavelength of 515 nm and normalized to the intensity with excitation at 408 nm. As it demonstrates in solution, the immobilized HPTS exhibits a positive pH-dependence in the normalized emission intensity with blue excitation with more than a tenfold increase between pH 5.2 and 8.2. The ratio of the intensity with excitation at 408 nm to the intensity with excitation at 468 nm was calculated at each pH for three identical, but separately constructed sensor assemblies to produce the calibration curve depicted in FIG. 7B. Each point represents the average intensity ratio of the three sensors with error bars of the standard deviation. In spite of slight differences in sensor orientation, thickness or local resin concentration, the standard error is consistently low, demonstrating the reproducibility of sensor construction and the robustness of the ratiometric technique.

In addition, the precision of these measurements indicates that the scatter described earlier is consistent and does not interfere with the operation of the sensor. The apparent pKa of the immobilized dye is approximately 7.7, slightly higher than that of HPTS in solution. This shift toward a more basic value is not surprising. Given that both the highly anionic sulfonic acid groups on the dye and the polyether segments of the PEG hydrogel are attractive to protons, the apparent pH inside the sensor matrix is reduced. The range of linearity of the HPTS-Dowex-PEG sensor extends from approximately 6.7 to 8.7. The increase in pKa is therefore favorable in terms of bioprocess measurement, as it corresponds to a working range that is consistent with that observed during many microbial and mammalian fermentations including *Escherichia coli* and *Klebsiella pneumoniae* (5, 19).

EXAMPLE 18

Figure 8:
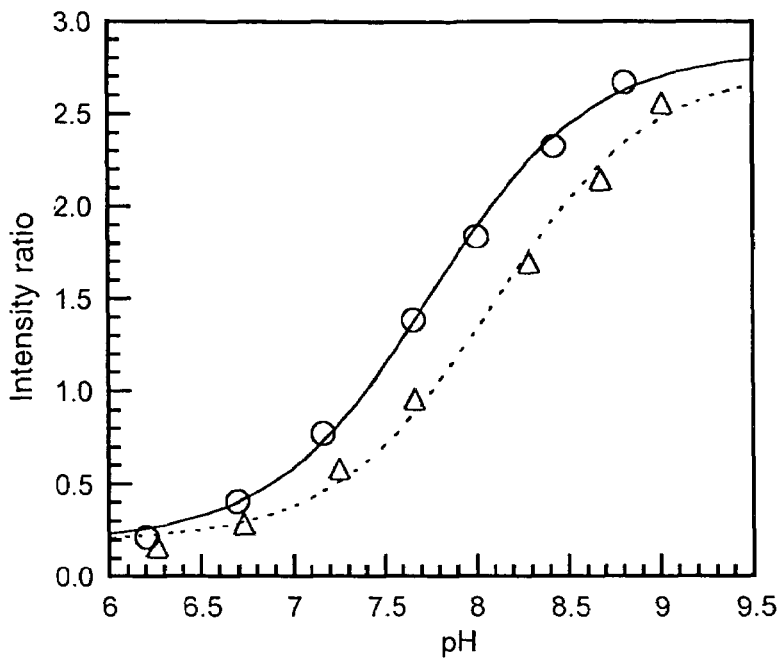
FIG. 8 depicts the calibration curve of the sensor measured in 0.15 M PBS (O) and 0.3 M PBS (Δ).

Performance of HPTS-Dowex-PEG Sensor Assembly Under Conditions of Varying Ionic Strength and Temperature The effect of various operating parameters on the performance of the HPTS-PEG-Dowex was evaluated. FIG. 8 compares the calibration curve of intensity ratio of a sensor assembly in 0.15 M and 0.3 M buffers. The intensity ratio of the HPTS-Dowex-PEG sensor is clearly affected by the ionic strength of the buffer, which is not surprising given the highly charged nature of HPTS. With increased ionic strength, the pKa of the immobilized dye and the range of linearity are slightly more basic, requiring a simple recalibration of the sensor at these conditions.

Figure 9:
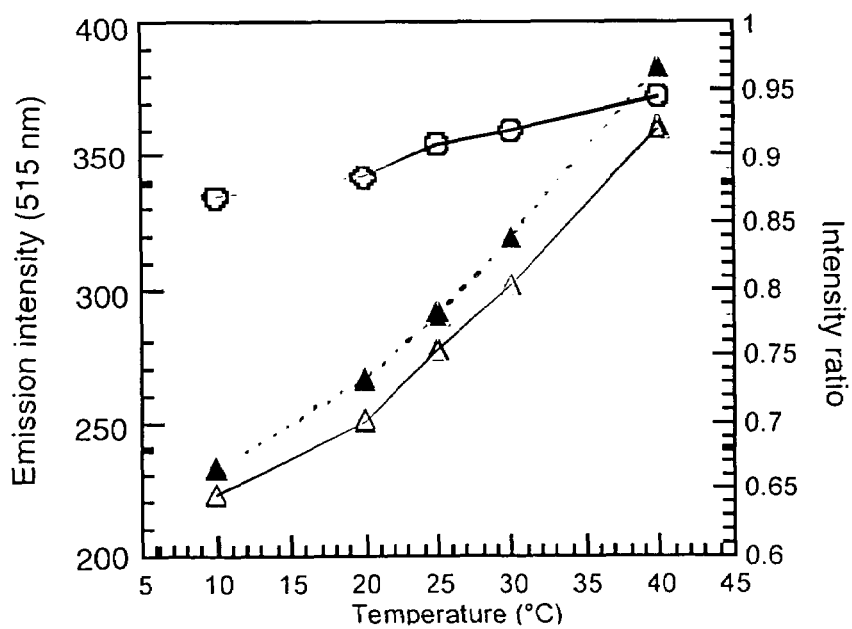
FIG. 9 depicts the effect of temperature on the properties of HPTS immobilized in PEG-Dowex with emission at 515 nm with excitaton at 408 nm (O) and 468 nm (Δ) and intensity ratio (▲).

The performance of the HPTS-PEG-Dowex sensor assembly is also sensitive to temperature. FIG. 9 depicts the emission intensities measured with excitation at 408 nm and 468 nm and the combined intensity ratio, as the temperature is increased between 10° C. to 40° C. At both excitation wavelengths, the increase in temperature corresponds to an increase in emission intensity. However, since the blue excitation wavelength of 468 nm responds with greater sensitivity, the increase in temperature also corresponds to an increase in intensity ratio.

Changes in temperature and ionic strength can influence the degree of hydration of both the Dowex resin and the PEG hydrogel and, therefore, the local dye concentration. However, such a change in swelling alone would be expected to affect both the UV and blue excitation peaks equally. Unexpectedly, this contradicts what is expected based on the increase in nonradiative decay at higher temperatures, indicating possible interactions between the dye and the immobilization resin. Since the sensor is targeted for use in bioprocesses that are largely temperature-controlled, the impact is minimal.

The effect of aging on sensor performance was also evaluated. Since PEG hydrogels must be stored hydrated to prevent cracking of the matrix, it is simportant to monitor the potential for leaching of HPTS into the soaking solution. Sensor assemblies were shielded from light and stored in deionized water for three weeks at ambient temperature. While loss of signal intensity was minor, less than 10%, and expected, owing to equilibrium leaching of HPTS from the matrix into the storage solution, there was no observable change in the sensor calibration curve. The sensor assembly was also exposed to 70% ethanol/water to determine the feasibility of this method of sterilization. Apart from temporary and reversible dehydration of the hydrogel matrix, no change in the performance of the sensor was detected.

The dynamic behavior of the sensor was investigated by pumping different pH buffers into the cuvette. The sensor was allowed to equilibrate in each buffer with constant, open-loop circulation from a larger reservoir while the excitation intensity ratio was monitored. The response time for a 95% change was approximately 9 minutes. While this is adequate for the purpose of bioprocess monitoring, the faster response times that are desirable for control schemes should be easily attained with a reduction in sensor thickness. The change in intensity ratio was completely reversible and could be cycled back and forth with no observable drift.

EXAMPLE 19

Use of HPTS-PEG-Dowex Sensor in a Hatch Fermentation

Figure 10:
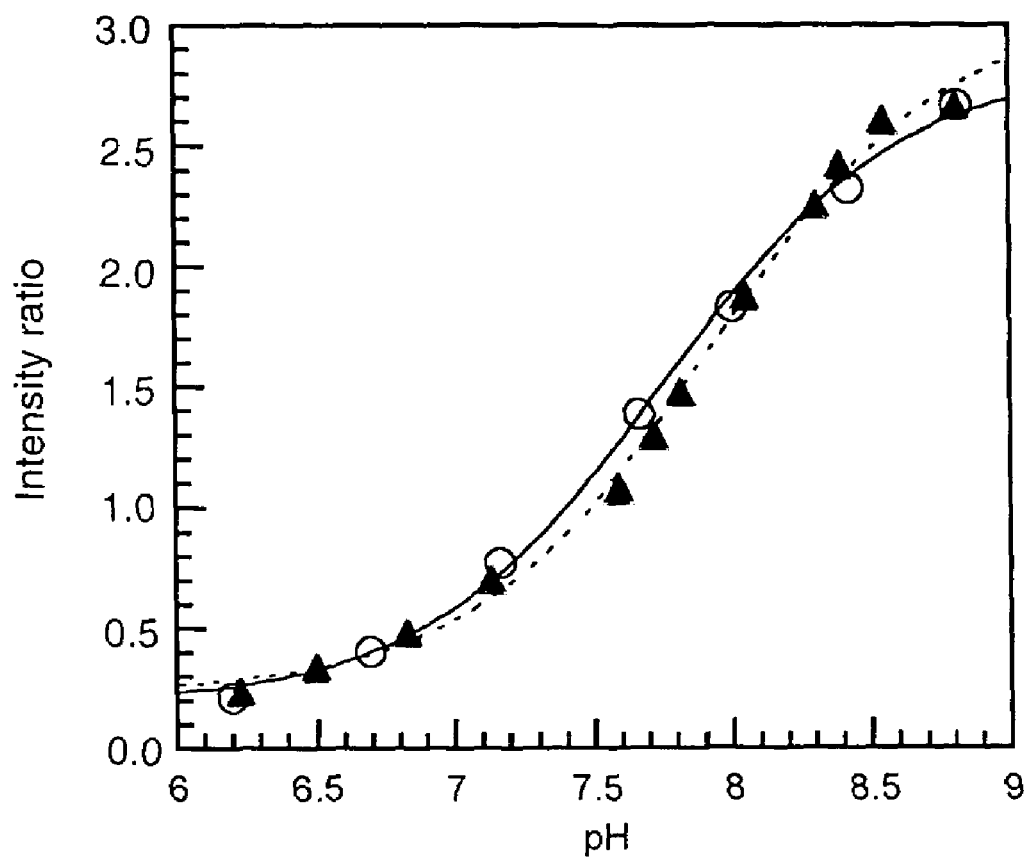
FIG. 10 depicts the intensity ratio measured in clear 0.15 M PBS (O) and in LB nutrient broth with *E. coli* (OD600 nm=0.25) (▲).

In preparation for use in a batch fermentation, the performance of the HPTS-PEG-Dowex sensor was evaluated in spent nutrient broth from an *Escherichia coli* fermentation. LB broth containing *E. coli* at an optical density of 600 nm of 0.25 was titrated to produce samples of varying pH, between 6 and 9. FIG. 10 compares the intensity ratio of the sensor measured in the spent media samples with the calibration curve in clear buffer. The experimental results in media are in good agreement with those in PBS, demonstrating that the presence of the opaque backing combined with the ratiometric technique eliminates the optical interference associated with media background fluorescence and scatter from the cell suspension.

A polystyrene disposable cuvette containing a sensor assembly was sterilized thoroughly with 70 v/v % ethanol solution, rinsed extensively in sterile water and mounted in the spectrophotometer. To prevent optical interference from the media beyond the edges the sensor, the outside of the cuvette was covered with black tape except for a small square that exposed the sensor. The fermentation broth was pumped into the cuvette and recirculated to the shake flask by a peristaltic pump operating at 40 mL/minute. The spectrophotometer recorded the emission intensity at 515 nm with excitation at 408 nm and 468 nm, at 1 minute intervals. At 20 minute intervals, samples of the media were removed and analyzed for pH using the ISFET probe and optical density at 600 nm using a Milton Roy Spectronic 401.

The PEG-Dowex sensor assembly was used to perform continuous on-line measurement of the pH during an *E. coli* fermentation. FIG. 11 depicts the pH of the media recorded online by the sensor and compared with that measured offline by a conventional pH probe. The optical density of the media is also shown as a measure of biomass production. The fermentation began at the initial media pH of 7.2 and remained relatively stable during the lag phase. As the cells enter the exponential growth phase, a dramatic increase in optical density is observed, followed by a corresponding increase in pH that is consistent with the accumulation of metabolic waste. The ensuing stationary phase is accompanied by a leveling in the pH at approximately 8.4. During the initial 8 hours of the fermentation, the pH recorded on line by the sensor was always in excellent agreement with that measured off line, with a maximum discrepancy of 0.08 pH units.

Furthermore, the raw intensities recorded by the sensor, as well as the calculated ratio, were remarkably stable with very little noise, in spite of the high flow rate of 40 mL/min and degree of mixing inside the cuvette. Toward the end of the fermentation, greater than 8.5 hours, a significant and consistent overprediction of approximately 0.15 pH units was observed. Examination of the used patch revealed evidence of microbial growth on the nside surface of the hydrogel, indicating that the patch had been poorly sealed to the transparency film. It is difficult to attach a highly swollen layer to a hydrophobic surface. The polyethylene tape used here to fix the patch in place may allow media to accumulate in stagnant areas between the hydrogel and the transparency film. Other methods of attachment may be more effective and could extend the lifetime of the sensor.

EXAMPLE 20

HPTS-pHEMA-METMA Sensor Assembly

The reaction mixture consisted of HEMA, METMA and EGDMA in a (10:1:0.8) volume ratio with 10 mg DMPA initiator per ml of HEMA. The mixture was sandwiched between two glass plates using aluminum spacer tape to maintain a gap width of approximately 100 µm. Free radical polymerization was initiated by exposure to a 100 W longwave UV spot lamp for 2 minutes. The polymer was hydrated overnight in deionized water and peeled from the glass plate.

A 1 cm square of pHEMA-METMA was placed in a solution of HPTS in 200 µM deionized water. The membrane was allowed to equilibrate for 24 hours with occasional stirring. Excess HPTS was removed by soaking in deionized water for a further 24 hours with several changes of the soaking solution. HPTS-membranes were mounted into polystyrene cuvettes for front face measurement as before, using 0.2 µm microfiltration membrane as a backing.

EXAMPLE 21

Excitation Spectra of HPTS-pHEMA-METMA Sensor in PBS at Varying pH

Figure 12A:
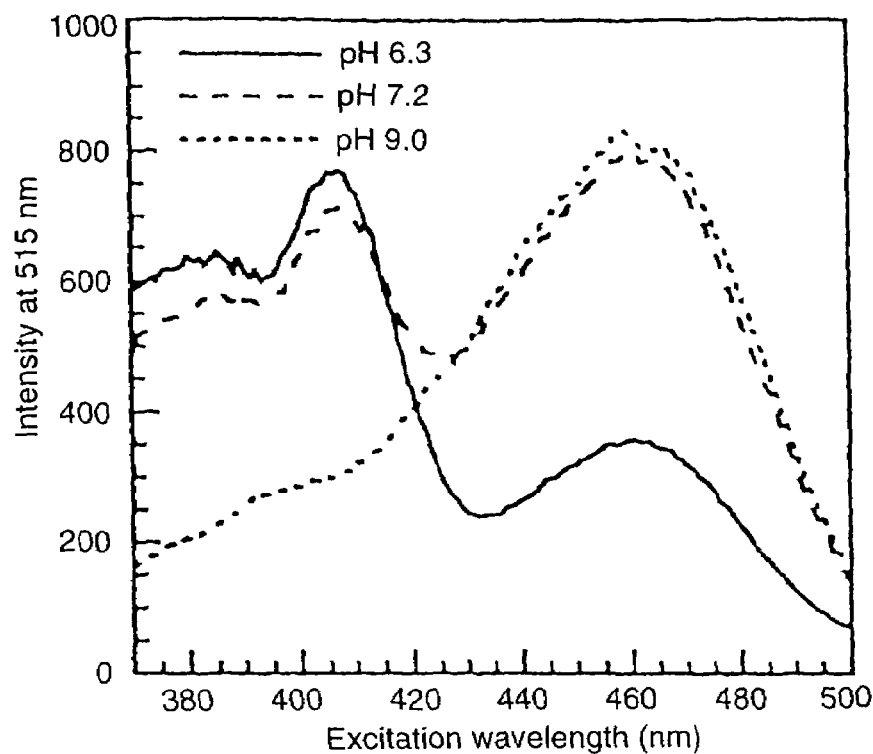
FIGS. 12A-12B depict the excitation spectra of HPTS immobilized in pHEMA-METMA membranes in PBS buffers (λemission=515 nm) (FIG. 12A) and the calibration curve of excitation intensity ratio (λemission=515 nm) (FIG. 12B).
Figure 12B:
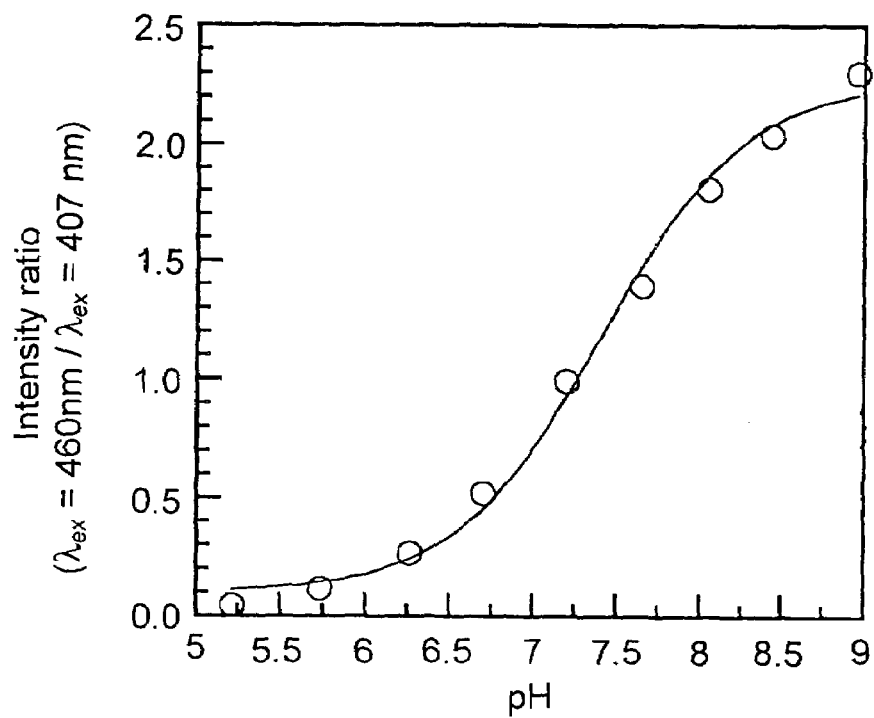

Hydrogel membranes of pHEMA-METMA are optically clear with good strength and flexibility. The cationic functionality incorporated via the comonomer results in visibly high HPTS uptake. Response times are on the order of a few minutes for a 200 µm thick sensor layer. FIG. 12A depicts the excitation spectra of the sensor layer in PBS buffers of varying pH. The spectrum of HPTS is preserved in the pHEMA-METMA layer and responds well to changes in pH ranging from about pH 6 to pH 9. FIG. 12B depicts a rough calibration curve.

The following references are cited herein:
1. Zen, J.-M. and G. Patonay (1991). "Near-infrared fluorescence probe for pH determination." *Analytical Chemistry* 63: 2934-2938.
2. Chan, C.-M, C.-S. Fung, et al. (1998). "Evaluation of a luminescent ruthenium complex immobilized inside Nafion as optical pH sensor." *Analyst* 123: 1843-1847.
3. Price, J. M., W. Xu, et al. (1998). "Polymer-supported pH sensors based on hydrophobically bound luminescent ruthenenium (II) complexes." *Analytical Chemistry* 70: 265-270.
4. Malins, C., H. G. Glever, et al. (2000). "Sol-gel immobilised ruthenium (II) polypyridyl complexes as chemical transducers for optical pH sensing." *Sensors and Actuators B* 67: 89-95.
5. Chan, C.-M., W. Lo, et al (2000), "Application of a luminescence-based pH optrode to monitoring of fermentation by *Klebsiella pneumoniae*." *Biosensors & Bioelectronics* 15: 7-11.
6. Clarke, Y., W. Xu, et al (2000). "Lifetime-based pH sensor system based on a polymer-supported ruthenium (II) complex." *Analytical Chemistry* 72: 3468-3475.
7. Xu, Z., A. Rollins, et al. (1998). "A novel fiber-optic pH sensor incorporating carboxy SNAFL-2 and fluorescent wavelength-ratiometric detection." *Journal of Biomedical Materials Research* 39: 9-15.
8. Song, A., S. Parus, et al. (1997). "High-performance fiber-optic pH microsensors for practical physiological measurements using a dual-emission sensitive dye." *Analytical Chemistry* 69: 863-867.
9. Wolfbeis, O. S., E. Fuerlinger, et al. (1983). "Fluorimetric analysis. I. Study on fluorescent indicators for measuring near neutral ('physiological') pH values." *Fresneius' Z. Anal. Chem.* 314(2): 119-124.
10. Agayn, V. I. and Dr. R. Walt (1993). "Fiber-optic sensor for continuous monitoring of fermentation pH." *Biotechnology* 72(6):6-9.
11. Lutty, G. A. (1978). "The acute intravenous toxicity of stains, dyes, and other fluorescent substances." *Toxical Pharmacol.* 44: 225-229.
12. Zhujun, Z. and W. R. Seitz (1984). "A fluorescence sensor for quantifying pH in the range from 6.5 to 8.5." *Analytical Chimica Acta* 160: 47-55.
13. Yafuso, M.; Hui, H. K., U.S. Pat. No. 4,798,738, (1989).
14. Kostov, Y., P. Harms, et al. (2001). "Low-cost micro-bioreactor for high-throughput bioprocessing.: *Biotechnol Bioeng* 72: 346-352.
15. Offenbacher, H., O. S. Wolfbeis, et al. (1986). "Fluorescence optical sensors for continuous determination of near-neutral pH values." *Sensor Actuator* 9: 73-84.
16. Schulman, S. G., S. Chen, et al. (1995). "Dependence of the fluorescence of immobilized 1-hydroxypyrene-3, 6,8-trisulfonate on solution pH: extension of the range of applicability of a pH fluorosensor." *Anal Chim Acta* 304: 165-170.
17. Gehrich, J. L., D. W. Lubbers, et al. (1986). "Optical fluorescence and its application to an intravascular blood gas monitoring system." *IEE TBio-med Eng* BME-33: 117-132.
18. Zhang, S., S. Tanaka, et al. (1995). "Fibre-optical sensor based on fluorescent indicator for monitoring physiological pH values." *Med Biol Eng Comput* 33: 152-156.
19. Shoichet, M. S., S. R. Winn, et al. (1993). "Poly(ethylene oxide)-grafted thermoplastic membranes for use as cellular hybrid bio-artificial organs in the central nervous system." *Biotechnology and Bioengineering* 43: 563-572.
20. Zhang, M., T. Desai, et al. (1998). "Proteins and cells on PEG immobilized silicon surfaces." *Biomaterials* 19: 953-960.
21. Peppas, N. A. and H. J. Moynihan (1987). Structure and physical properties of poly(2-hydroxyethyl methacrylate) hydrogels. *Hydrogels in Medicine and Pharmacy, Volume II: Polymers*. N. A. Peppas. Boca Raton, Fla., CRC Press Inc.
22. Holata, J., S. Sevcik, et al. (1974). "Chemical transformations of polymers. XVI Preparation and splitting of poly(methacryloyloxyethyltrimethylammonium hydroxide)." *Journal of Polymer Science Symp.* 47: 335-343.
23. Haughland, R. P. (2000). *Handbook of Fluorescent Probes and Research Chemicals* Molecular Probes, Inc. Eugene, Oreg.
24. Zhang, S., S. Tanaka, et al. (1995). "Fibre-optical sensor based on fluorescent indicator for monitoring physiological pH values." *Medical and Biological Engineering & Computing* 33: 152-156.
25. Tsien, R. Y. (1989). "Fluorescent indicators of ion concentrations." *Methods Cell Biol* 30: 127-156.
26. Kermis, H. R., Y. Kostov, et al. (2002). "Dual excitation ratiometric fluorescent pH sensor for noninvasive bioprocess monitoring: Development and application." *Biotechnol Prog* 18: 1047-1053.
27. Cruise, G. M., D. S. Scharp, et al. (1998). "Characterization of permeability and network structure of interfacially photopolymerized poly(ethylene glycol) diacrylate hydrogels." *Biomaterials* 19: 1287-1294.
28. Albert, A. and Seargeant, E. P. The Determination of Ionization Constants. Chapman and Hall, London (1971).

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:
1. A ratiometric fluorescent pH sensor comprising:
a fluorescent dye immobilized within a polymer matrix comprising,
6-methacryloyl-8-hydroxy-1,3-pyrene disulfonic acid (MA-HPDS) covalently bound within a p(ethylene glycol) hydrogel matrix; or
8-hydroxy,1,3,6-pyrene trisulphonic acid trisodium salt (HPTS) ionically bound within a p(ethylene glycol) diacrylate monomer that is polymerized around an anionic exchange resin; said fluorescent dye exhibit- ing a shift in excitation wavelength with a corresponding shift in pH in the local environment of said fluorescent dye and said polymer matrix comprising a front surface and a back surface;

a siloxane-based comonomer; embedded in the polymer matrix, a means of optically isolating said polymer matrix comprising said fluorescent dye; and an adhesive means on the front surface of the polymer matrix.

2. The ratiometric fluorescent pH sensor of claim 1, further comprising a cross-linking agent.

3. The ratiometric fluorescent pH sensor of claim 2, wherein the cross-linking agent is triethylolpropane triacrylate or ethylene glycol dimethacrylate.

4. The ratiometric fluorescent pH sensor of claim 1, wherein the optically isolating means is a microfiltration membrane.

5. The ratiometric fluorescent pH sensor of claim 1, wherein the adhesive means is an adhesive tape, a hydrophobic adhesive substrate or a transfer adhesive.

6. The ratiometric fluorescent pH sensor of claim 5, wherein said adhesive tape is polyethylene tape or said hydrophobic adhesive substrate is a silicon rubber substrate or an acrylate-functional adhesive.

7. The ratiometric fluorescent pH sensor of claim 1, wherein the fluorescent dye comprising the sensor responds to a shift in pH within a range of about pH 6.0 to about pH 9.0.

8. The ratiomeric fluorescent pH sensor of claim 1, wherein the sensor is sterilized.

9. The ratiometric fluorescent pH sensor of claims 1, wherein the sensor comprises a patch, assembly of said sensor patch comprising placing the adhesive means on a flat surface;

adhering the front surface of said polymer matrix comprising said fluorescent dye to the adhesive means; and covering the back surface of sai polymer matrix with the optically isolating means.

10. A system for non-invasive monitoring of pH comprising:

a reaction vessel in which to monitor the pH;

the ratiometric fluorescent pH sensor of claim 1 wherein the front surface of said pH sensor adheres to the reaction vessel via said adhesive means;

a means for delivering a first pH-sensitive excitation maximum wavelength to the front surface of said fluorescent pH sensor;

a means for delivering a second pH-sensitive excitation maximum wavelength to the front surface of said fluorescent pH sensor;

a means for detecting maximum emission intensity of a wavelength emitted from said fluorescent pH sensor at both of the first and second pH-sensitive excitation maxima wavelengths; and a means for evaluating a ratio of the first and second maximum emission intensities as pH.

11. The system of claim 10, further comprising means for closed-loop feedback control of the system.

12. The system of claim 10, wherein said delivery means is a diode emitting light within the ultraviolet wavelength range or within the blue wavelength range.

13. The system of claim 10, wherein said detecting means is a photodiode.

14. A ratiometric fluorescent pH sensor comprising:

a fluorescent dye, 8-hydroxy-1,3,6-pyrene trisulphonic acid trisodium salt (HPTS), exhibiting a shift in excitation wavelength with a corresponding shift in pH in the local environment of said fluorescent dye;

a poly(2-hydroxyethyl methacrylate)-co-(methacryloyl ethyltrimethyl ammonium chloride) (pHEMA-METMA) copolymer hydrogel matrix, said HPTS immobilized therein via ionic binding, said pHEMA-METMA copolymer hydrogel matrix comprising a front surface and a back surface;

a means of optically isolating said pHEMA-METMA copolymer hydrogel comprising said HPTS; and an adhesive means on the front surface of the polymer matrix.

15. The ratiometric fluorescent pH sensor of claim 14, further comprising a comonomer, a cross-linking agent or a combination thereof.

16. The ratiometric fluorescent pH sensor of claim 14, wherein the comonomer is a siloxane-based monomer.

17. The ratiometric fluorescent pH sensor of claim 16, wherein the cross-linking agent is triethylolpropane triacrylate or ethylene glycol dimethacrylate.

18. The ratiometric fluorescent pH sensor of claim 14, wherein the optically isolating means is a microfiltration membrane.

19. The ratiometric fluorescent pH sensor of claim 14, wherein the adhesive means is an adhesive tape, a hydrophobic adhesive substrate or a transfer adhesive.

20. The ratiometric fluorescent pH sensor of claim 19, wherein said adhesive tape is polyethylene tape or said hydrophobic adhesive substrate is a silicon rubber substrate or an acrylate-functional adhesive.

21. The ratiometric fluorescent pH sensor of claim 14, wherein the fluorescent dye comprising the sensor responds to a shift in pH within a range of about pH 6.0 to about pH 9.0.

22. The ratiomeric fluorescent pH sensor of claim 14, wherein the sensor is sterilized.

23. The ratiometric fluorescent pH sensor of claims 14, wherein the sensor comprises a patch, assembly of said sensor patch comprising placing the adhesive means on a flat surface;

adhering the front surface of said polymer matrix comprising said fluorescent dye to the adhesive means; and covering the back surface of sai polymer matrix with the optically isolating means.

24. A system for non-invasive monitoring of pH comprising:

a reaction vessel in which to monitor the pH;

the ratiometric fluorescent pH sensor of claim 14 wherein the front surface of said pH sensor adheres to the reaction vessel via said adhesive means;

a means for delivering a first pH-sensitive excitation maximum wavelength to the front surface of said fluorescent pH sensor;

a means for delivering a second pH-sensitive excitation maximum wavelength to the front surface of said fluorescent pH sensor;

a means for detecting maximum emission intensity of a wavelength emitted from said fluorescent pH sensor at both of the first and second pH-sensitive excitation maxima wavelengths; and a means for evaluating a ratio of the first and second maximum emission intensities as pH.

25. The system of claim 24, further comprising means for closed-loop feedback control of the system.

26. The system of claim 24, wherein said delivery means is a diode emitting light within the ultraviolet wavelength range or within the blue wavelength range.

27. The system of claim 24, wherein said detecting means is a photodiode.

* * * * *